United States Patent [19]

Schulze, Jr.

[11] Patent Number: 4,671,297

[45] Date of Patent: Jun. 9, 1987

[54] METHOD AND APPARATUS FOR MONITORING INFANTS ON ASSISTED VENTILATION

[76] Inventor: Karl F. Schulze, Jr., Pelham, N.Y.

[21] Appl. No.: 791,183

[22] Filed: Oct. 25, 1985

[51] Int. Cl.⁴ .............................................. A61B 5/08
[52] U.S. Cl. .................................. 128/716; 128/721; 128/725; 128/204.23
[58] Field of Search .......... 128/1 B, 716, 725, 204.23, 128/202.12, 205.26, 721–724

[56] References Cited

U.S. PATENT DOCUMENTS 3,896,792 7/1975 Vail et al. .............................. 128/725
4,459,982 7/1984 Fry .................................. 128/204.23

FOREIGN PATENT DOCUMENTS 2812447 3/1978 Fed. Rep. of Germany ......................... 128/204.23

Primary Examiner—Kyle L. Howell
Assistant Examiner—Randy Citrin
Attorney, Agent, or Firm—Pennie & Edmonds

[57] ABSTRACT

An apparatus and method are described for measuring variables associated with the ventilation of infants during assisted ventilation. The infant is placed in a plethysmograph and various sensor means are used to measure flow of gas into and out of the plethysmograph and infant respiration. The outputs of the sensor means are supplied to a minicomputer system for processing. From this data, ventilator breaths are discriminated from infant breaths.

10 Claims, 4 Drawing Figures

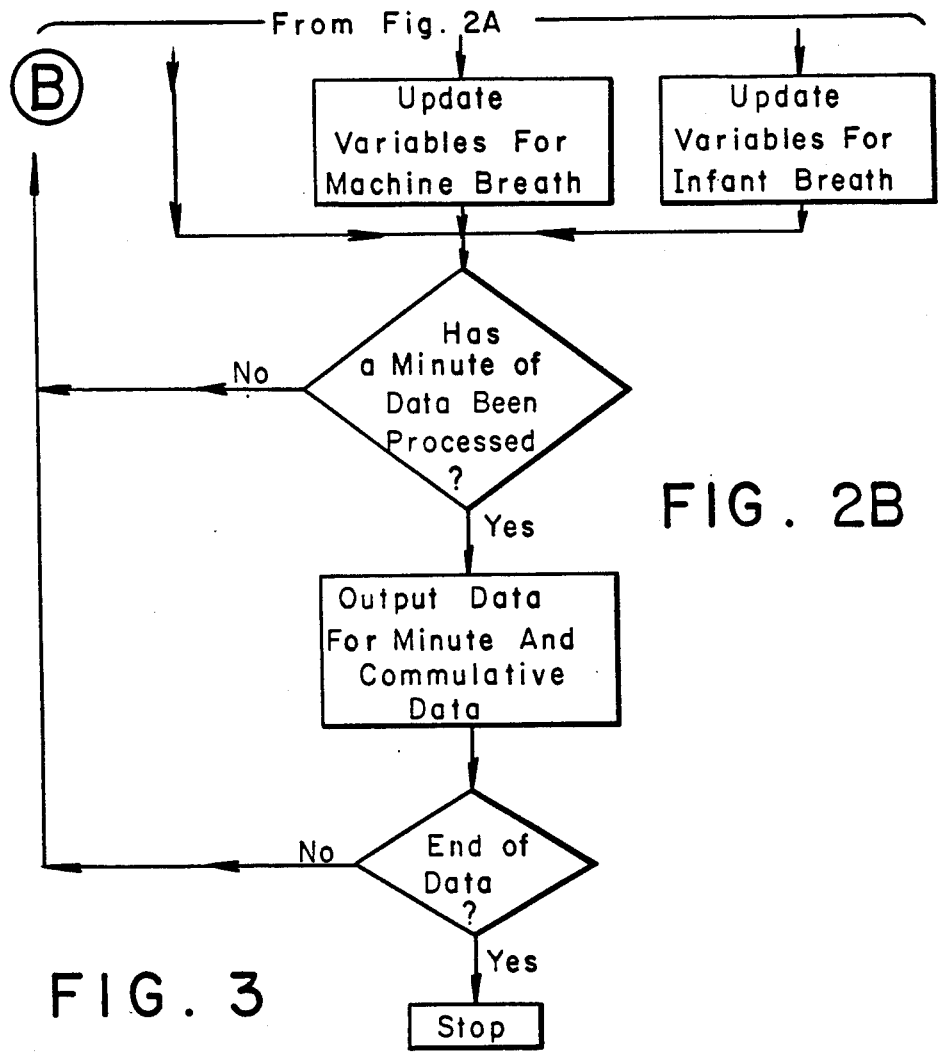
FIG. 2B
FIG. 3
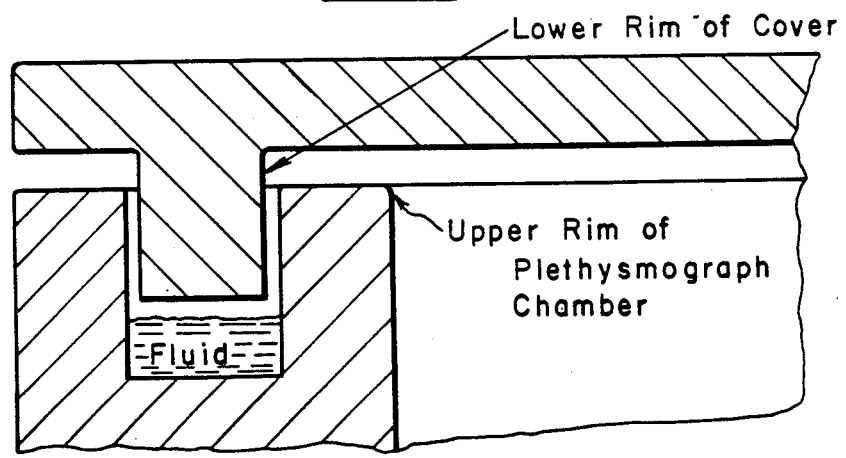

METHOD AND APPARATUS FOR MONITORING INFANTS ON ASSISTED VENTILATION

BACKGROUND OF THE INVENTION

A portion of the disclosure of this patent document contains material to which a claim of copyright protection is made. The copyright owner has no objection to the electrophotographic reproduction by anyone of the patent document or the patent disclosure, as it appears in the Patent & Trademark Office patent file or records, but reserves all other copyright rights whatsoever.

Mechanical ventilatory assistance is now widely accepted as an effective form of therapy for respiratory failure in the neonate. Mechanical ventilators are a conspicuous and fundamental part of tertiary neonatal care. When on assisted ventilation, the newborn infant becomes part of a complex interactive system which is expected to provide adequate ventilation and gas exchange.

The overall performance of the assisted ventilatory system is determined by both physiological and mechanical factors. The physiological determinants, over which the physician has relatively little control, change with time and are difficult to define. These include the nature of the pulmonary disease, the ventilatory efforts of the infant, and many other anatomical and physiological variables. Mechanical input to the system, on the other hand, is to a large extent controlled and can be reasonably well characterized by examining the parameters of the ventilator pressure pulse. Optimal ventilatory assistance requires a balance between physiological and mechanical ventilation. This balance should insure that the infant is neither overstressed nor oversupported. Insufficient ventilatory support would place unnecessary demands on the infant's compromised respiratory system. Excessive ventilation places the infant at risk for pulmonary barotrauma and other complications of mechanical ventilation.

Intelligent management of ventilatory assistance in the neonate requires that information about the performance of the overall system be available to the clinician. Instrumentation for continuous monitoring of infants on assisted ventilation, as well as certain component variables of ventilation are known, "Instrumentation for the Continuous Measurement of Gas Exchange and Ventilation of Infants During Assisted Ventilation", K. Schulze, M. Stefanski, J. Masterson, et al., *Critical Care Medicine*, Vol 11, No. 11, pp. 892–896 (1983). However, at the present time, physicians rely largely on intermittent measurement of arterial blood gases to monitor the overall effects of the system on gas exchange. These measurements, while important in clinical care, have several limitations. Data acquired by such measurements provides little information about the separate contributions of the infant and the mechanical ventilator to overall ventilation and gas exchange of the infant.

Absent this information, the effects of changes in ventilator support are not as readily observable. For example, it is frequently desirable to monitor how an infant responds to respiratory therapy such as positive end expiratory pressure ("PEEP") therapy. To administer this therapy, the ventilator increases resistance to expiratory gases, thus decreasing the burden on an infants lungs.

In addition, arterial blood gas measurements are available only intermittently, which makes both trends and abrupt changes in clinical condition of the patient difficult to recognize. Continuous values are appreciably more helpful in describing the time course of changes in the patient's clinical condition.

When acquiring measurements of infant ventilation for research purposes, it customary to place the infant in a container known as a plethysmograph. With the exception of openings used for respiratory support of the infant and quantitative measurement of the infant's respiration, the interior of the plethysmograph must be isolated from the external environment. Also, for these quantitative measurements to be useful in patient care, it is desirable to configure the plethysmograph such that the sensors are in a relatively stable environment and the infant monitored remains warm and undisturbed. At the same time, however, it is essential that the infant be accessable in a very short period in the event that some emergency arises.

SUMMARY OF THE INVENTION

In accordance with the present invention, a method and apparatus are described herein for providing continuous measurement of infant ventilation during assisted ventilation, which is particularly adapted for providing information about the respective contributions to ventilation by the infant and the ventilation mechanism. In the presently preferred embodiment, the apparatus comprises a heated plethysmograph in which an infant is placed, a pneumotachometer and a differential pressure transducer for detecting infant respiration, a pressure transducer for measuring pressure at an infant's airway in order to discriminate the infant's breaths from ventilator breaths, data recording means for storing data obtained by said pressure transducers and time data and a preprogrammed minicomputer system for processing and storing data acquired by the aforementioned components. In another embodiment, the invention comprises a second pneumotachometer and a second differential pressure transducer for determining when ventilator breaths occur.

Details of the performance of this system have been described in Karl Schulze, et al., "Computer Analyses of Ventilatory Parameters For Neonates On Assisted Ventilation," *IEEE Engineering In Medicine And Biology Magazine* Vol. 3, No. 3, pp. 31–33 (Sept. 1984) which is incorporated herein by reference.

In an alternate embodiment, data from the differential pressure transducer and from the airway pressure transducer or second differential pressure transducer are processed on-line and real-time monitoring data is displayed.

An additional feature of the present invention is the isolation of the plethysmograph chamber by the use of a fluid seal. A reservoir of fluid fills a trough which extends around the perimeter of the plethysmograph. This trough receives the lower rim of the plethysmograph cover and an airtight seal is thereby formed with said fluid and lower rim of plethysmograph cover. Optionally, an extremely thin, elastic and pliable membrane covers the trough to prevent the fluid therein from escaping. In this embodiment, the seal is formed between the membrane and the lower rim of the plethysmograph cover.

Still another feature of the invention is that the plethysmograph, which is ordinarily utilized as a highly specialized research tool, is adapted for clinical patient care. The plethysmograph is heated and ready access to the infant can be accomplished due to the fluid seal arrangement. Furthermore, the monitoring data obtained through use of the invention is of great clinical value.

BRIEF DESCRIPTIONS OF THE FIGURES

These and other objects, features and advantages of the invention will be more readily apparent from the following detailed description of the preferred embodiment in which:

FIGS. 2A and 2B are flowcharts for the presently preferred embodiment of the computer program for processing data obtained in accordance with the invention.

FIG. 3 depicts the water seal used to isolate the interior of the plethysmograph from the external environment.

DETAILED DESCRIPTION OF THE PREFERRED EMBODIMENT

Figure 1:
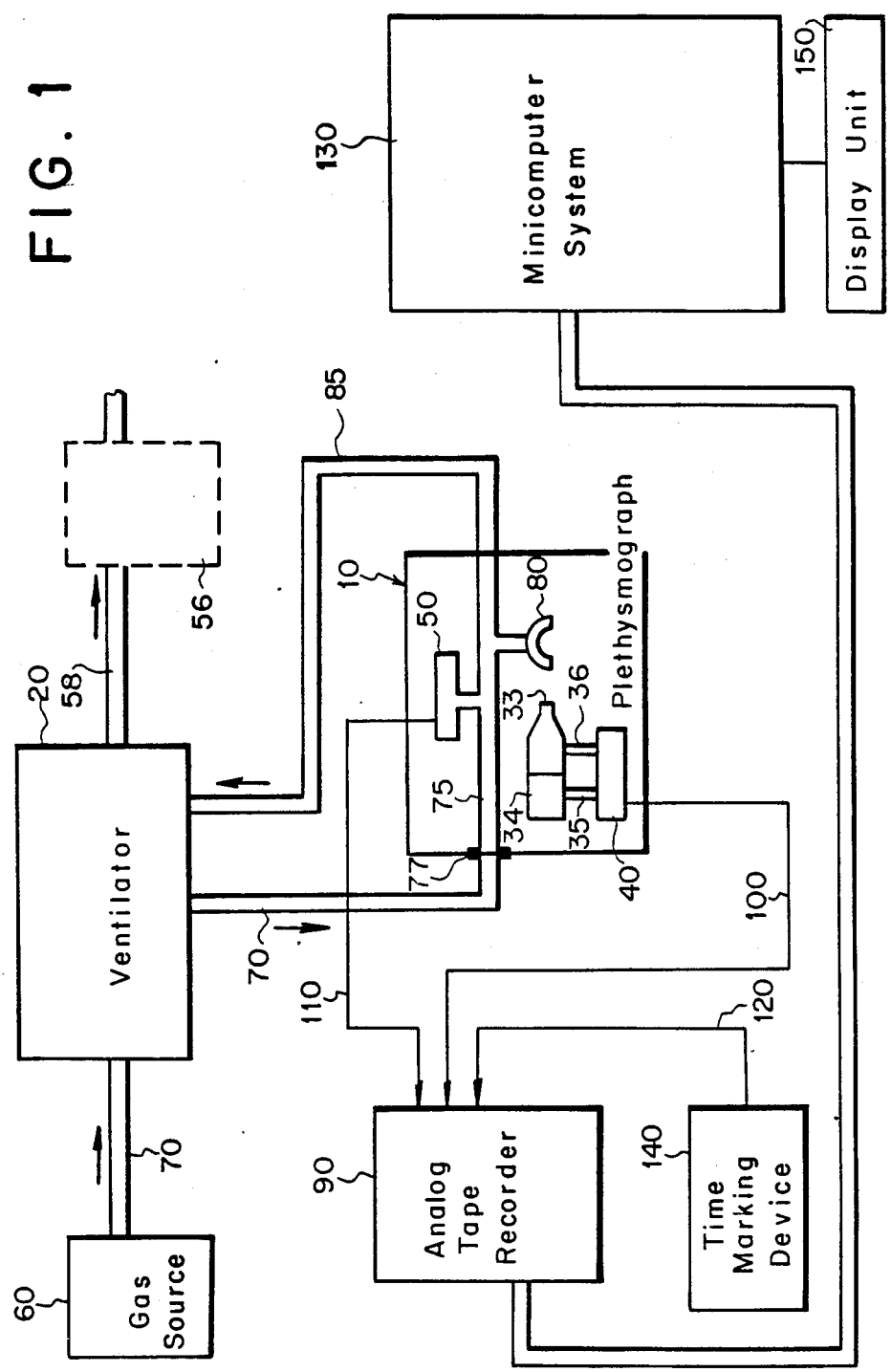
FIG. 1 is a block diagram showing an overview of the presently preferred embodiment of the apparatus as employed in a system for ventilating an infant.
Figure 2A:
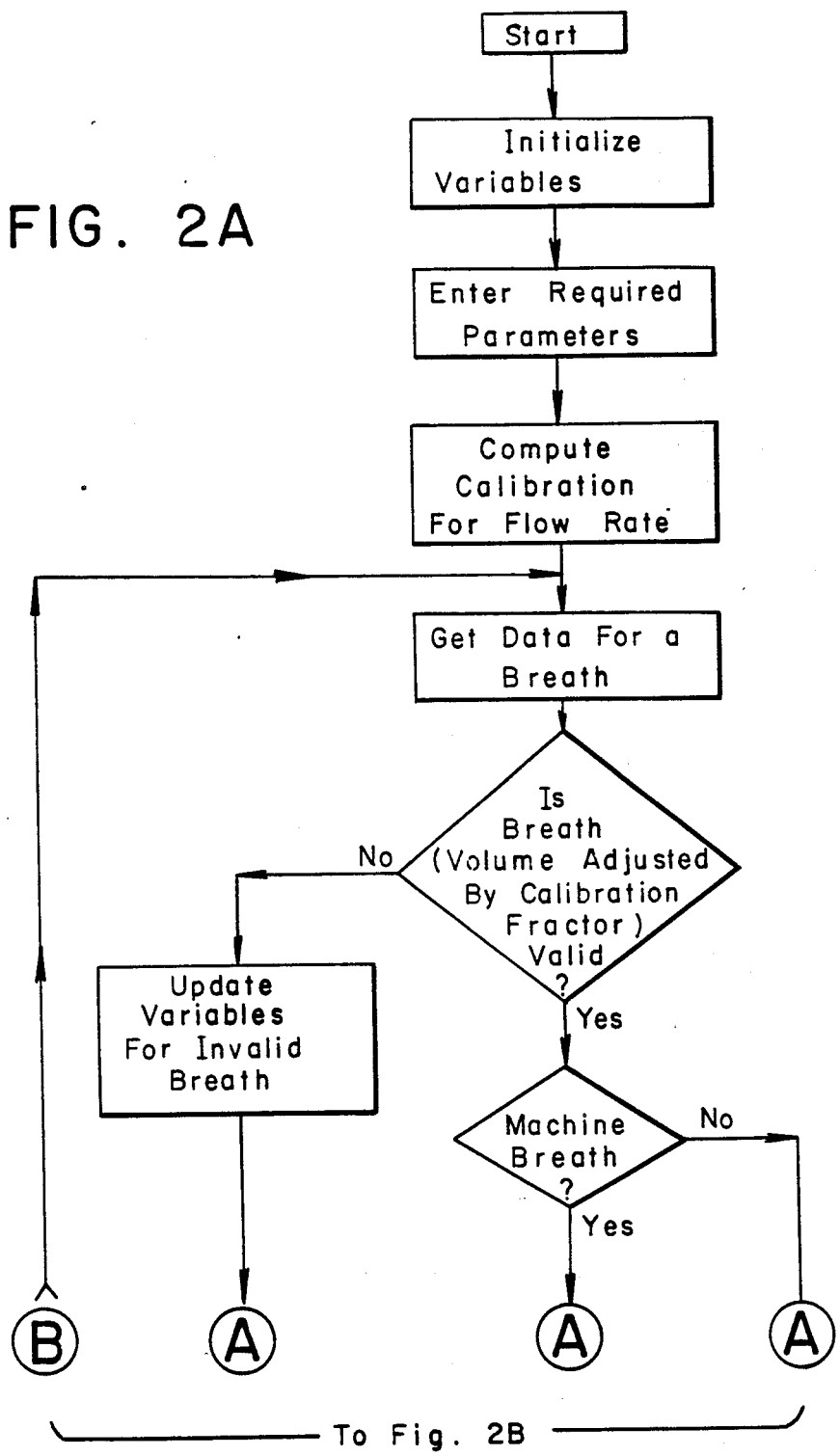

As shown in FIG. 1, the presently preferred embodiment of the apparatus comprises a plethysmograph 10 in which an infant to be monitored is placed, a ventilator 20 for ventilating the infant, a pneumotachometer 30 and a differential pressure transducer 40 for measuring gas flow into and out of plethysmograph 10, and a pressure transducer 50 for detecting pressure in the infant's airway. A gas source 60 feeds ventilator 20 via pipe 70 with gas for ventilation of the infant. This gas, typically an oxygen-nitrogen mixture, is provided to the infant in the phethysmograph 10 through pipe 75 and an endotracheal tube 80. Pipe 85 carries expiratory gases back to ventilator 20. When ventilator 20 fires to respirate the infant, the ventilator occludes pipe 85 so that gas provided to the infant by pipes 70, 75 will be forced through endotracheal tube 80 and into the infant's airway.

Analog data provided by differential pressure transducer 40 and pressure transducer 50, together with timing data, is provided to recording device 90 by lines 100, 110, 120. Minicomputer 130, digitizes this analog data and stores it on magnetic tape. The digital data is then processed by minicomputer 130 to obtain total tidal volume, volume due to infant respiratory efforts and volume due to the effects of mechanical ventilation. These values are then displayed by the minicomputer on a suitable display unit 150. This unit may provide both digital and analog displays as well as a continuous record in the form of a strip chart or circular chart recorder. Advantageously, all of the equipment depicted in FIG. 1 is mounted on a movable cart so that the infant can readily be moved, for example, for emergency treatment, without altering either his respiratory support or the monitoring thereof.

In the presently preferred embodiment, plethysmograph 10 comprises an appropriately heated plexiglass box capable of containing an infant. The interior atmosphere of the plethysmograph is isolated from the exterior environment, except for one or more ports for respiration of the infant and coupling of pneumotachometer 30, described below. Illustratively, pipes 70, 75 are coupled together at port 77. Pneumotachometer 30 illustratively comprises a chamber divided in half by a pliable and semi-permeable screen with one chamber having a tapered port 33 for receiving pressure and another chamber communication with the environment outside the piethysmoraph. Although many appropriately selected commercial pneumotachometers will be suitable for use in the practice of the invention, a description of the pneumotachometer used in the presently preferred embodiment may be found in "Pneumotechograph For Use With Patients During Spontaneous or Assisted Ventilation," G. Gregory, J. Kitherman, *Journal of Applied Physics,* Vol. 31, p. 766 (Nov. 1971).

Pressure variations occurring on the interior of the plethysmograph, such as those resulting from expansion and contraction of an infant's chest, are reflected in the pneumotachometer. Pneumotachometer 30 and differential pressure transducer 40 are advantageously located inside the plethysmograph, with port 33 of the pneumotachometer open to the plethysmograph interior. Placement of pneumotachometer 30 and transducer 40 inside the plethysmograph reduces the potential for inaccuracies in the data acquired due to temperature differences between said elements and the plethysmograph. Tubes 35, 36 are each coupled to one half of the pneumotachometer chamber. Differential pressure transducer 40 senses the pressure in the two halves of the pneumotachometer chamber via tubes 35, 36 and outputs an analog signal to line 100 showing the amount and direction of gas flow into and out of plethysmograph 10. Illustratively, differential pressure transducer 40 comprises a Validyne DP45 pressure transducer.

In the presently preferred embodiment, amount and direction of gas flow are reflected by the magnitude and polarity, respectively, of the output signal from transducer 40. Thus, inspiration and expiration result in different polarity outputs from the transducer. Pipe 75 is coupled to endotracheal tube 80, which is in turn inserted into the airway of the infant. Pressure transducer 50, preferably be a Novametrix airway monitor device, is located in the endotracheal tube and senses pressure in the infant's airway. The transducer 50 outputs an analog signal indicating said pressure to line 110. In an alternate embodiment the function of pressure transducer 50 is instead accomplished by a second pneumotachometer and pressure transducer 56. These components detect pressure changes in tube 58.

To correlate in the time domain the signals produced by differential pressure transducer 40 and pressure transducer 50, a time-marking device 140, preferably a Datum 1000 Time Code Generator device, continuously outputs data to line 120 showing the current time. Lines 100, 110, 120 are coupled to an analog data recording device 90, preferably an HP 3968 FM Analog tape recorder, which records the signals output by differential pressure transducer 40, pressure transducer 50 and time-marking device 140.

Minicomputer system 130, in the presently preferred embodiment, comprises an HP 1000 F-series minicomputer, an HP 2313 digital converter, a magnetic tape drive and other standard peripheral devices. Minicomputer system 130 receives signals from analog data recording device 90 when said device is actuated to play back recorded data and utilizes the analog-to-digital converter to digitize this data. The magnetic tape drive stores the digitized data.

In accordance with one embodiment of the present invention, digital data stored on the magnetic tape drive is processed by the minicomputer to obtain total tidal volume as follows. First, a calibration factor for pneumotachometer 30 is determined by injecting and withdrawing a premeasured volume of gas into and out of plethysmograph 10 and processing flow data obtained by penumotachometer 30 and transducer 40 during this procedure.

The calibration factor is helpful in compensating for inaccurate flow measurements such as those resulting from thermal transients in the plethysmograph. Integration of inspiration flow data is then corrected by multiplying the value from each data point.

In the presently preferred embodiment, the output signal of a differential pressure transducer 40 is positive during inspiratory flow and negative during expiratory flow. Ideally, the integration of positive value inspiratory flow data should equal the integration of negative expiratory flow data, since, over time, the volume of gas into and the volume of gas out of the infant's lungs are ordinarily the same. To obtain the calibration factor, a predetermined amount of flow data obtained during the sample injection and withdrawal of gas is integrated. A bias value, indicating the degree to which inspiration and expiration differ, is then obtained by dividing this integral by the product of the number of flow data samples integrated and the sampling rate.

Next, the positive inspiratory data, only, are integrated, with the bias value being subtracted from each sample of flow data as it is included in the integration computation. The volume of gas which was injected in the calibration procedure, in cubic centimeters, is then divided by the adjusted integration to determine the calibration factor. The data obtained during monitoring is then processed.

While in the presently preferred embodiment, a calibration factor is obtained one time, prior to the processing of data acquired during monitoring, it is also in accordance with the invention to calibrate periodically during monitoring. An important feature of this embodiment of the invention is to calibrate using data gathered over a sufficiently long period such that irregularities occurring within one or two breaths are not mistaken for a general inaccuracy in measurement which is susceptible to correction by calibration. In this embodiment, the predetermined volume of gas injected into and withdrawn from plethysmograph 10 is sufficiently large such that ventilator and infant breaths will comprise a relatively small percentage of total gas flow. A predetermined amount of flow data obtained from transducer 50 during injection and withdrawal of the gas is integrated and a real-time bias value is then obtained by dividing this integration by the product of the number of flow data samples obtained and the sampling rate. This real-time bias value is an index of the degree to which inspiration and expiration differ, and is useful to physicians as an estimate of such factors as endotracheal tube leakage and thermal transients. Optionally, the realtime bias value also serves as an alarm indicator when the endotracheal tube is slipping from the infant's airway. The bias value also gives the physician an indication of the stability of the monitoring system.

The inspiratory flow data is then integrated using the real-time bias value as described above in connection with pre-monitoring calibration. A calibration factor is then obtained by first determining the sum of the injected volume and the average difference between said volume and the integration of the inspiratory data. That sum is then divided by the integration of the inspiratory data which was corrected by the real-time bias value, with the result being a real-time calibration factor.

It is anticipated, however, that some flow data which appears to represent breaths will actually be the result of factors other than respiratory activity. Movement by the infant, for example, may generate such flow data. In order to obtain an accurate measurement of breath tidal volume, actual breath must be discriminated from noise. Illustratively, the flow data acquired during the relevant period is tested to determine whether it meets the following criteria: the data contains only two polarity changes, a negative-to-positive polarity change followed by a positive- to-negative polarity change; the flow data must indicate that the breath was of at least a minimum duration and a minimum tidal volume; and the highest value data point of the flow data must be of at least a minimum value.

In the presently preferred embodiment, the criteria for a valid breath, either ventilator induced or infant, are that it must be at least 0.1 seconds in duration and must result in a tidal volume of at least 0.5 cubic centimeters. Furthermore, the amplitude of the flow data must be at least plus or minus three standard deviations of the breath amplitudes for the previous one minute period.

Tidal volume of valid breaths is computed by integrating the inspiratory flow data obtained during those breaths and multiplying the result by the calibration factor. Illustratively, for each minute of monitoring, the tidal volume, duration and maximum amplitude of each inspiratory volume or breath and the total tidal volume and frequency of breaths are stored in an external memory file for minute total data.

In accordance with the present invention, the minute total data is indexed to and processed in conjunction with time data and pressure data from pressure transducer 50 to determine whether each breath is the result of infant respiratory efforts or is due to mechanical ventilation. For each minute of monitoring, tidal volume of each breath is referenced to airway pressure data obtained from pressure transducer 50 during the same period. More particularly, under control of the computer program set forth in Appendix I, minicomputer system 130 compares each inspiratory volume, within a given minute, with the airway pressure data obtained from pressure transducer 40, or alternatively with the data output by second transducer 56, during the period that the inspiratory volume was collected.

The data associated with a given breath is then copied into one of two different data files, preferably located in external storage memory, depending on whether the inspiratory volume associated with that data was due to an infant breath or resulted from mechanical ventilation. An inspiratory volume which occurs simultaneously with a change in airway pressure which exceeds a predetermined magnitude is stored in a file for mechanical ventilator breaths. In the presently preferred embodiment, the predetermined change in airway pressure is approximately 20 mm. of Hg., but this value is subject to change depending upon the ventilator output pressure. Conversely, a breath occurring without any such change in airway pressure is stored in a file for infant breaths. In the event that pressure data from pneumotachometer and pressure transducer 56 is used instead of data from transducer 50, comparison is made between the breath volume and the data output by transducer 50 during the period of the breath. In this case the program detects a drop in pressure in tube 58 caused by ventilator 20 occluding tube 85.

These two files, therefor, contain the number, duration and tidal volume of ventilator and infant breaths occurring within each minute as well as the maximum amplitude of the flow signal for each breath.

In the presently preferred embodiment, the FORTRAN language computer program shown in Appendix I, suitable for execution on an HP 1000 minicomputer, is used to process the digitized data stored on the tape drive of minicomputer system 130. It will be noted that the program calls various subroutines such as NUMR, OPENF, CLOCK, TIME, VSUM and other standard routines. These external routines are standard calls for the Hewlett-Packard standard Fortran compiler associated with the HP 1000 F-series minicomputer. The program in Appendix I uses the term "respiration data" to refer to the data acquired by pneumotachometer 30 and differential pressure transducer 40. "Flow data" in said program refers to data acquired by airway pressure transducer 50, or alternatively second transducer 56.

Although the invention has been described as an apparatus and method wherein data is accumulated on a continuous basis for a predetermined period and is then loaded into a minicomputer system for processing, it will be apparent to those skilled in the art that an on-line data accumulation, processing and display is equally contemplated by the invention. In this embodiment lines 100, 110 are coupled to an analog-to-digital conversion means having at least two input channels which in turn outputs digital data to minicomputer system 130. Breath volume, duration, and frequency is determined in real-time and classification of ventilator versus infant breath is accomplished after each breath. Time marking device 140 is eliminated and timing functions are instead performed by standard minicomputer software. Display of the ventilation characteristics of the infant in real-time is similarly contemplated.

One advantage to this embodiment is that changes in infant respiration can be rapidly perceived and appropriate action taken. It is thus further in accordance with this embodiment to continually determine a bias value, (as described above in connection with calibration of the pneumotachometer) using actual inspiratory and expiratory flow data obtained during monitoring of the infant. If the bias value exceeds a predetermined level, an alarm is sounded to alert the clinician to the possibility of an endotracheal tube leak or that some other potentially dangerous condition such as slippage of said tube, exists.

An additional feature of the invention is shown in FIG. 3 and comprises a plethysmograph chamber having an upper rim with a trough filled with fluid extending around the upper rim and a cover having a lower rim extending downward around the perimeter of the cover. The lower rim of the cover is positioned such that the trough in the upper rim of the plethysmograph chamber receives the lower rim of the cover, thus forming a seal between the fluid in the trough and said lower rim. In an alternative embodiment, the fluid in the trough is covered by a very thin flexible and elastic membrane which prevents the fluid from escaping.

With the plethysmograph sealed in this fashion, an infant therein can be accessed very quickly in the event some emergency arises.

APPENDIX 1

TIDAL VOLUME COMPUTATION PROGRAM

```
1    FTN4
2    C
3    C   Copyright, Karl P. Schulze, Jr., 1985.
4    C   ....................................................
5    C
6            PROGRAM TIDAL    (3,80),TIDAL VOLUME COMPUTATION
7    C
8    C    PURPOSE
9    C         COMPUTE BREATH-BREATH ( INTERVAL,TIDAL VOLUME,DURATION,AMPLITUDE)
10   C         , MINUTE TIDAL VOLUME OF PURE BABY,S BREATHS ,
11   C         , MINUTE TIDAL VOLUME OF VENTILATOR,S BREATHS.
12   C
13   C    DESCRIPTION OF INPUT PARAMETERS
14   C         1) INPUT FILE NAME , BLOCK SIZE , PARAMETER #
15   C         2) PARAMETER # OF RESP. AND FLOW SIGNALS
16   C         3) DIRECTION OF PEAK FLOW SIGNAL
17   C         4) CONDITIONS FOR THE BREATH   PATTERN RECOGNITION
18   C              MINUMUM DURATION OF BREATH      for exAMPLe :    0.1 SEC
19   C              MINIMUM VOLUME OF BREATH                         0.5 CC
20   C         5) ENTER THE DISCONNECTED PERIOD
21   C         6) ENTER THE PNEUMOTACH POLARITY [+ , -]
22   C         7) ENTER PARAMETER # FOR TIME CODE
23   C         8) INTEGRATION PERIOD , SAMPLING INTERVAL
24   C         9) CALIBRATION FACTOR
25   C         10) CALIBRATION VOLUME
26   C         11) IF CALIBRATION FACTOR = 0 ,
27   C              THAT MEANS WE MUST COMPUTE THE CALIBRATION FACTOR ,
28   C              SO ENTER THE START AND STOP RECORDS OF CALIBRATION .
29   C              -----       -----       ----
30   C         12) IF ICFLG = YES , COMPUTE THE CALIBRATION FACTOR ONLY .
31   C              IF ICFLG = NO  , COMPUTE THE CAL. FACTOR AND TIDAL VOLUME ALSO.
```

```
32    C          13) OUTPUT FILE NAME
33    C          14) PROCESSING REC. # OF START AND STOP
34    C          15) COMMENTS
35    C              ... CHECK THE START TIME FOR TCG GENERATION
36    C              ... CHECK THE FIRST FLOW SIGNAL
37    C                  ( IT MUST BE AFTER THE MINUTE MARK )
38    C       * METHOD
39    C          1) INTEGRATE THE RESPIRATORY DATA OVER ONE MINUTE
40    C          2) COMPUTE BIAS LINE = INTEGRATION AREA / ONE MINUTE
41    C          3) RECOGNIZE BREATH SIGNAL BY SCANNING UPPER PART OF BIAS LINE
42    C          4) INTEGRATE THE BREATH SIGNAL
43    C          5) DECIDE THAT SIGNAL IS BABY PURE BREATH OR VENTILATOR FIRE
44    C          6) WRITE THE PARAMETERS IN DISC FOR FURTHER ANALYSIS
45    C
46    C          * 5 POINTS MOVING AVERAGE USED FOR FILTERING
47    C          * AMPLITUDE INCLUDED FOR VALID BREATH CRITERIA  04/19/85
48    C          * PEAK FLOW SIGNAL DISTANCE FROM BASELINE COMPUTATION ALSO ..
49    C  05/29/85 MODIFY...  FOR CORK OUT PERIOD
50    C    1) ABS(BIAS-OLDBIAS) SHOULD BE LESS THAN 10 .
51    C    2) DISTANCE=MAX-MIN  SHOULD BE GREATER THAN 10 .
52    C    3) MEAN - STD  FOR CRITERIA
53    C    4) CRFRQ     10MSEC = 40  ,   30 MSEC = 20
54    C   ...............................................
55    C
56           DOUBLE PRECISION MNSTRT , STADDR , BEFORE , CURRNT
57           INTEGER IDATA(1500),INAMR(10),IFILE(10),ITIME(4),IDCB(272),
58         1    LBUFF(40),IBUFF(10),POLP,JTIME(5),TFILE(3),FILE(10),PKCNT,
59         2    IBUF2(100),IDCB2(528),RECNUM,COUNTR,PKREC(30),PKPTR(30)
60         3    ,QUEPNT,SGNCNT,BOUND,STKPNT,IDUMMY(4)
61         4    ,STORG(200) , NSTORG ,PKREC1(30) , PKPTR1(30)
62         5    ,VENRE1      , VENPT1 ,VENCNT
63           REAL BUF2(100),MINVOL,MACSUM,MINDUR,MINVOL,RESPDT(10),FLOWDT(10)
64           REAL TABL(-6,120),MINAMP,SAVOL(160,2),PRSTAB(10)
65           COMMON  SAMPLE
66           EQUIVALENCE (IBUF2,BUF2)
67           DATA POLP/1/,IPOS2,OUTCNT /1,0./,MINDUR,MINVOL/0.1,0.3/
68           DATA IDUMMY/17*999/
69    C
70    C
71    C    INITIALIZATION
72    C    --------------
73    C        WRITE (1,6211)
74    C6211 FORMAT(/" ** < FLOW SIGNAL DIVIDED  BY 5 FOR DECREASING > **"///)
75    C    ... BABY HARRIS    ...
76    C        GAIN = .143
77    C        YINCPT = 5.714
78    C
79           SUBTOT = 0
80           ENDMRK = 999.
81           NTAB = 0
82           DURCNT = 0
83           VOLCNT = 0
84           AMPCNT = 0
85           DISTNC = 0
86           OLDAMP = 0
87           TOTCNT = 0
88           DSTCNT = 0
89           NBRETH = 0
90           NDATA = 0
91           MACHBR = 0
92           OLDRSP = -1
93           SAVE1 = 0
94           SAVE2 = 0
95           IFRQ = 0
96           BASE = 30000
97           AMPMIN = 32767
98           FLWDST = 100
99           SAVDST = 100
100          SUMVEN = 0.0
101          SQUVEN = 0.0
102          VENCNT = 0
103   C
104   C    INPUT FILE NAME AND FORMAT
105   C    --------------------------
106   C
107          WRITE (1,1011)
108   1011 FORMAT(/"ENTER PRINT DEVICE NUMBER   ... 6 OR 2B OR 3B _")
```

```
109         READ (1,*) LUOUT
110         WRITE(1,10)
111         READ(1,12) LBUFF
112         I = 1
113         CALL NAMR(IFILE,LBUFF,ITLOG(LEN),I)
114         CALL NAMR(INAMR,LBUFF,LEN,I)
115         LRECL = INAMR(1)
116         CALL NAMR(INAMR,LBUFF,LEN,I)
117         NPARAM = INAMR(1)
118         BEFORE = NPARAM * 10
119         CALL OPENF(IDCB,IERR,IFILE,0,IFILE(5),IFILE(6),256)
120         IF(IERR) 900,15,16
121   15    IF(IFILE(4).EQ.1) CALL CNUMD(IFILE(1),IFILE)
122   16    WRITE(1,20)
123         READ(1,*) LRESP
124         WRITE (1,22910)
125   22910 FORMAT(/" PARAMETER # OF FLOW SIGNAL ? _")
126         READ (1,*) IREF
127         WRITE(1,22915)
128   22915 FORMAT(/"FLOW SIGNAL PEAK IS downward OR upward ?   D or U ")
129         READ (1,22917) BOUND
130   22917 FORMAT(1A1)
131         IF (BOUND.EQ.1HU) FLWSGN = 1
132         IF (BOUND.EQ.1HD) FLWSGN = -1
133         MINFLW = 32767
134   C
135   C     ( EVERY SIGNAL WILL BE CONVERTED TO UPWARD PEAK PROCESSING )
136   C
137   C
138         WRITE(1,11301)
139   11301 FORMAT(/"initial value for VALID Dur.=0.1sec , Vol=0.3cc ")
140         CRDUR = 0.1
141         CRVOL = 0.3
142   C
143   C     POLARITY ( - )  MEANS  BABY INSPIRATION .
144   C              ( + )         BABY EXPIRATION .
145         WRITE (1,8051)
146   8051  FORMAT(/" ENTER POLARITY OF RESP SIGNAL   ... + OR - _")
147         READ (1,8052) I
148   8052  FORMAT(A1)
149         IF(I.EQ.1H-) POLP = -1
150         WRITE(1,24)
151         READ(1,*) ITCR
152         WRITE (1,2401)
153   2401  FORMAT(/"ENTER START TIME  ... HOUR , MINUTE  ORDER _")
154         READ (1,*) ITIME(2) , ITIME(3)
155         ITIME(3) = ITIME(3) - 1
156         IF (ITIME(3) .EQ.-1)ITIME(2) = ITIME(2) - 1
157         IF (ITIME(3) .EQ.-1)ITIME(3) = 0
158         WRITE(1,26)
159   C *   PERIOD ... TOTAL UNIT INTEGRATION TIME
160   C *   SAMPLE ... SAMPLING RATE
161         READ(1,*) PERIOD,SAMPLE
162         IF (SAMPLE .LE. 0.025)  CRFRQ = 20
163         IF (SAMPLE .EQ. 0.010)  CRFRQ = 40
164         NPTS = LRECL
165   C
166   C *   NMDATA IS DATA COUNT FOR ONE MINUTE
167   C *   NUMSEC IS NUMBER OF DATA WITH ONE SECOND UNIT
168   C *   STEP   IS X INCREMENT IN TIDAL VOLUME INTEGRATION
169   C
170
171         NMDATA = PERIOD/SAMPLE
172         NMDAT1 = NMDATA * 7.0 / 6.0
173         NUMSEC = 1 / SAMPLE
174         MINDST = 2 * NUMSEC
175         STEP = 0.5*SAMPLE
176         WRITE(1,30)
177         READ(1,*) FCALIB
178         IF (FCALIB.GT.0) GO TO 59
179         WRITE(1,34)
180         READ(1,*) CALVOL
181   C
182   C     START & STOP OF CAL. VALUES
183         WRITE(1,36)
184         READ(1,*) IRP1,IRP2
185         WRITE(1,38)
```

```
185         READ(1,12) ICFLG
186         IF(ICFLG.EQ.2HYE) GO TO 79
187   C
188   C     OUTPUT FILE NAME
189   C
190   59    WRITE(1,40)
191         READ(1,12) LBUFF
192         I = 1
193         CALL NAMR(FILE,LBUFF,ITLOG(LEN),I)
194         CALL NAMR(IBUF2,LBUFF,LEN,I)
195         IRECL2 = IBUF2(1)
196         CALL OPENL(7,IERR,FILE,2HOL,FILE(5),FILE(6))
197         CALL OPENL(4,IERR,5HPRSFIL,3HOLD,0,0)
198         CALL OPENL(5,IERR,5HBABYBR,3HOLD,0,0)
199         IF(FILE(4).EQ.1) CALL CNUMD(FILE(1),FILE)
200         IF(IERR.GE.0) GO TO 5020
201         GO TO 900
202   5020  WRITE(1,50)
203   C
204   C
205         READ(1,*) NFIRST,NREC
206         LSTREC = NFIRST+NREC-1
207         IF(NREC.GT.0) GO TO 64
208         IEOF = 1
209         NREC = 32767
210         LSTREC = 32767
211   64    WRITE(1,65)
212         READ(1,12) LBUFF
213   C
214   C     COMPUTE PNEUMOTACH CALIBRATION FACTOR
215   C     -----------------------------------
216   C
217   79    IF(FCALIB.GT.0.) GO TO 100
218         DO 90 IPASS=1,2
219         CALL POSNT(IDCB,IERR,IRP1,1)
220         IF(IERR.LT.0) GO TO 900
221         SUM = 0.
222         XPTS = 0.
223         RECNUM = IRP1-1
224         INIT = 0
225   72    RECNUM = RECNUM+1
226         IF(RECNUM.GT.IRP2) GO TO 88
227         CALL READF(IDCB,IERR,IDATA,LRECL,LEN)
228         IF(IERR.LT.0 .OR. LEN.EQ.-1) GO TO 900
229         IPTR = 0
230         IF(INIT.EQ.1) GO TO 75
231         OLDRSP = -POLP*IDATA(IRESP+IPTR) - BIAS
232         INIT = 1
233   75    RESP = POLP*IDATA(IRESP+IPTR) - BIAS
234         IF(IPASS.EQ.2 .AND. RESP.LT.0.) RESP =0
235         SUM = SUM + STEP*(RESP+OLDRSP)
236         OLDRSP = RESP
237         XPTS = XPTS+1
238         IPTR = IPTR + NPARAM
239         IF(IPTR-LRECL) 75,72,72
240   88    BIAS = SUM/(XPTS*SAMPLE)
241   90    CONTINUE
242         FCALIB = CALVOL/SUM
243         WRITE (1,5160) BIAS,SUM
244   5160  FORMAT(/"CAL. BIAS= ",F10.0,"    INTEGRATION AREA = ", F10.3)
245         WRITE(1,92) FCALIB,CALVOL
246         IF(ICFLG.EQ.2HYE) GO TO 399
247   C
248   C     INITIALIZE THE SLOW CODE ROUTINE
249   C     & PEAK FLOW SIGNAL DISTANCE FROM BASELINE
250   C     & POSITION TO STARTING RECORD
251   C     -----------------------------------
252   C
253   100   CALL POSNT(IDCB,IERR,NFIRST,1)
254         IF(IERR.LT.0) GO TO 900
255         INITTC = 0
256         MAXFLW = -32767
257         MINFLW =  32767
258         NUMFLW =  1
259         IF(ITCR.EQ.0) GO TO 180
260         DO 165 I=NFIRST,LSTREC
261         CALL READF(IDCB,IERR,IDATA,LRECL,LEN)
```

```
263            IF(IERR.LT.0 .OR. LEN.EQ.-1) GO TO 900
264            IPTR = 0
265    158     ITEMP = IDATA(ITCR+IPTR)
266            IF (NUMFLW .EQ. NMDATA) GO TO 159
267            NUMFLW = NUMFLW + 1
268            FLOW  = IDATA(IREF+IPTR)
269            IF (I.EQ.NFIRST .AND. IPTR.EQ.0) GO TO 1580
270            GO TO 1584
271    1580    CONTINUE
272            DO 1582 IN = 1,10
273    1582    FLOWDT(IN) = FLOW
274            QUEPNT = 10
275    1584    FLOWDT(QUEPNT) = FLOW
276            QUEPNT = QUEPNT + 1
277            IF (QUEPNT.GT.10) QUEPNT = 1
278            CALL VSUM (FLOWSM,FLOWDT,1,10)
279            FLOW = FLOWSM / 10
280            IF (FLOW.GT.MAXFLW) MAXFLW = FLOW
281            IF (FLOW.LT.MINFLW) MINFLW = FLOW
282    159     IF(ITEMP.LE.0) GO TO 160
283            CALL CLOCK(ITEMP,IFLAG,ITIME,INITTC)
284            IF(IFLAG.EQ.1) GO TO 170
285    160     IPTR = IPTR + NPARAM
286            IF(IPTR.LE.LRECL) GO TO 158
287    165     CONTINUE
288            ITCR = 0
289            WRITE(1,168)
290            GO TO 160
291    C
292    170     CONTINUE
293            ONESEC = 1 / SAMPLE
294            CURBL  = I
295            CURRC  = ITCR + IPTR
296            MINMRK = CURRC - ((ONESEC-1)*NPARAM)
297            IF (MINMRK.GT.0) GO TO 175
298            CURBL = I - 1
299            MINMRK = MINMRK + LRECL
300    175     CONTINUE
301            CURRC = MINMRK
302            FLOWLV = 24
303            WRITE(LUOUT,30320) CURBL , MINMRK , FLOWLV
304    30320   FORMAT(/"FIRST MINUTE MARK START AT ", 2I5,
305           *          /"PEAK FLOW AMPL. FROM BASE. ",  I5)
306    C       WRITE(1,4190) FLOWLV
307    4190    FORMAT(/" ** PEAK FLOW SIGNAL FORM BASELINE --- ",I4)
308            ITCR = 0
309            GO TO 160
310    C
311    C       INTEGRATE THE PNEUMOTACH SIGNAL
312    C       -------------------------------
313    C
314    180     MINUTE = 1
315            ICNT5 = 1
316            IPASS = 1
317            CALL POSNT(IDCB,IERR,NFIRST,1)
318            IF(IERR.LT.0) GO TO 900
319            MINUTE = 1
320            CALL TIME(JTIME)
321            WRITE(LUOUT,304)JTIME,LBUFF,(IFILE(I),I=1,3),
322           1 LRECL,NPARAM,NFIRST,NREC,PERIOD,FCALIB,SAMPLE
323            WRITE (LUOUT,3041)
324            WRITE (LUOUT,11311)
325    11311   FORMAT(5X," h: m: s",3X,"  BABY    VENT. ",14X,"BABY    VENT"
326           *,5X,"DUR  VOL  AMP"/
327           */,5X,6 ("_"),3X,16("_"),14X,10"_",5X,13"_"//)
328    C
329    200     IPTR = LRECL
330            RECNUM = NFIRST-1
331            COUNTR = 1
332            INIT = 0
333            SUM = 0.
334            AMPL = -1000
335            MACHIN = 0
336            MACSUM = 0
337            SQUMAC = 0
338            IFLOW = 0
339            SUMDUR = 0
```

```
340             SUMAMP = 0
341             SUMVOL = 0
342             SQUDUR = 0
343             SQUVOL = 0
344             SQUAMP = 0
345             NBRETH = 0
346             BIAS = 0
347             IFIRST = 0
348       C
349       C     GET NEXT RECORD
350       C     ---------------
351       C
352   204     RECNUM = RECNUM+1
353             IF(RECNUM.GT.LSTREC) GO TO 310
354       C *
355   11309 CONTINUE
356             CALL READF(IDCB,IERR,IDATA,LRECL,LEN)
357             IF (LEN.EQ.-1) GOTO 310
358             IF(IERR.LT.0) GO TO 901
359       C * SKIP THE DATA BEFORE MINUTE-START-MARK .
360             IF (RECNUM.LT.CURBL) GO TO 204
361             IF (RECNUM.GT.CURBL) GO TO 205
362             IPTR = MINMRK
363             GO TO 207
364   205     IPTR = 0
365   207     CONTINUE
366       C
367       C     INTEGRATE THE RESPIRATORY SIGNAL
368       C     --------------------------------
369       C       POLP   = POLARITY
370       C
371             IF(INIT.EQ.1) GO TO 210
372       C *   IF INIT = 0 , INITIALIZE FOR THE INTEGRATION
373             IBIT = IPASS - 1
374             IF(MINUTE.EQ.1)OLDRSP = (-POLP*IDATA(IRESP+IPTR) + IBIAS)
375             IF(MINUTE.GT.1)OLDRSP = (1-IBIT) * SAVE1 + IBIT * SAVE2
376             IF (IPASS.EQ.2) GO TO 31140
377             SAVREC = RECNUM
378             SAVPTR = IPTR
379             MNSTRT = RECNUM * 10000. + IPTR
380             GO TO 31150
381   31140 NPOS = SAVREC
382             CALL POSNT (IDCB,IERR,NPOS,1)
383             IF (IERR.LT.0) STOP 7777
384             CALL READF(IDCB,IERR,IDATA,LRECL,LEN)
385             RECNUM = NPOS
386             IPTR = SAVPTR
387   31150 INIT = 1
388             IF (IFIRST .NE. 0 ) GO TO 31155
389             DO 31153  MV = 1,5
390             RESPDT(MV) =         IDATA(IRESP+IPTR)
391             FLOWDT(MV) =         IDATA(IREF +IPTR) * FLWSGN
392   31153 CONTINUE
393             MINFLW = 32767
394             IFIRST = 1
395             QUEPNT = 1
396   31155 CONTINUE
397   210     CONTINUE
398             RESPDT(QUEPNT) = IDATA(IRESP+IPTR)
399             FLOWDT(QUEPNT) = IDATA(IREF +IPTR) * FLWSGN
400             QUEPNT = QUEPNT + 1
401             IF (QUEPNT.GT.5 ) QUEPNT = 1
402             CALL VSUM(RESPSM,RESPDT,1,5 )
403             CALL VSUM(FLOWSM,FLOWDT,1,5 )
404             AVGRSP = RESPSM / 5.
405             AVGFLW = FLOWSM / 5.
406             IDATA(IRESP+IPTR) = AVGRSP
407             IDATA(IREF +IPTR) = AVGFLW
408             RESP = POLP*IDATA(IRESP+IPTR) - BIAS
409             RERESP = POLP * IDATA(IRESP+IPTR)
410       C
411       C     RESP IS TREND-REMOVED RESPIRATORY SIGNAL
412       C       USED FOR TIDAL VOLUME COMPUTATION
413       C       IF RESP > 0 , STILL BREATHING PERIOD .
414       C
```

```
415  C      RERESP IS TREND-INCLUDED RESPIRATORY SIGNAL
416  C         USED FOR THE MAXIMUM AMPLITUDE DETECTION DURING ONE BREATH.
417  C
418  C      ** PASS = 1 PROCESS  **
419  C
420         IF (IPASS.EQ.2) GO TO 30610
421         GAPFLW = GAPFLW + 1
422         IF (COUNTR.LE.NMDATA) SUM = SUM + STEP * (RESP + OLDRSP)
423         IF (COUNTR.EQ.NMDATA) SDSTNC = DISTNC
424         IF (COUNTR.EQ.NMDATA) SAVFLW = FLWDST
425         FLOW = IDATA (IREF+IPTR)
426         DISTNC = DISTNC + 1
427  C      ACTPRS = FLOW * GAIN + YINCPT
428  C  ---------
429         NSTORG = NSTORG + 1
430         NSTORG = MOD (NSTORG , 200)
431         IF (NSTORG .EQ. 0) NSTORG = 200
432         STORG(NSTORG) = FLOW
433  C  ---------
434         IF (FLOW .GT. MINFLW) GO TO 5142
435         IFRQ = 0
436         MINFLW = FLOW
437         GO TO 5170
438  5142   CONTINUE
439         IFRQ = IFRQ + 1
440         RANGE = (FLOW - MINFLW)
441         IF (IFRQ.LT.CRFRQ) GO TO 5170
442         IF (RANGE .LT. FLOWLV) IFRQ = 0
443         IF (IFRQ .EQ. 0) GO TO 5170
444         IF (FLOW.LT.OLDFLW) GO TO 5146
445         TOPCNT = 0
446         GO TO 5170
447  5146   TOPCNT = TOPCNT + 1
448         IF (TOPCNT .EQ. 2) GO TO 5169
449         GO TO 5170
450  C      IF (GAPFLW .LT. DISTNC ) GO TO 5170
451  5169   CONTINUE
452         BEFORE = VENRE1 * 10000. + VENPT1
453         CURRNT = RECNUM * 10000. + IPTR
454         SUBT = CURRNT - BEFORE
455         IF (DISTNC .GT. MINDST .AND.
456        *     SUBT    .GT. MINDST ) GO TO 51691
457         TOPCNT = 0
458         IFRQ = 0
459         MINFLW = 32767
460         GO TO 5170
461  51691  CONTINUE
462         STADDR = RECNUM * 10000. + IPTR
463         IF (MNSTRT .LE. STADDR) GO TO 51692
464         MINFLW = 32767
465         IFRQ = 0
466         GO TO 5170
467  51692  PKCNT = PKCNT + 1
468         IFRQ = 0
469         SVPTR = IPTR
470         SVREC = RECNUM
471         IPTR = IPTR
472         IF (IPTR.GE.0) GO TO 6274
473         RECNUM = RECNUM - 1
474         IPTR = IPTR + LRECL
475  6274   CONTINUE
476         STADDR = RECNUM * 10000. + IPTR
477         IF (MNSTRT .LE. STADDR ) GO TO 6275
478         RECNUM = SVREC
479         IPTR   = SVPTR
480  6275   CONTINUE
481         COMREC = RECNUM
482         COMPTR = (IREF+IPTR)
483         PKREC1(PKCNT) = RECNUM
484         PKPTR1(PKCNT) = COMPTR
485  C  ---------
486  C              CHECK THE BEGINNING OF PRESSURE SIGNAL
487         ICNT = 0
488         ISTCHK = NSTORG
489         RMIN = 32767
490         MAX =-32767
491         DO 7010 I =1 , 200
```

```
492            IF (I .EQ. 31) GO TO 7015
493     C      WRITE (1,6310) I ,ISTCHK,STORG(ISTCHK) ,OLDPRS,RMIN,MAX
494     6310   FORMAT(/" PRESSURE CHECK " ,2I5,4F5.1)
495            IF (STORG(ISTCHK) .GT. MAX) MAX = STORG(ISTCHK)
496     6311   CONTINUE
497            IF (STORG(ISTCHK) .LT. RMIN) RMIN = STORG(ISTCHK)
498            IF ( I .GT.10) GO TO 7000
499            OLDPRS = STORG(ISTCHK)
500            GO TO 7005
501     7000   DIFF = STORG(ISTCHK) - OLDPRS
502            IF (DIFF .LT. 0) GO TO 7003
503            IF (IABS(MAX) .EQ. 32767    .OR.
504          *     IABS(RMIN).EQ. 32767     )  GO TO 7004
505            DIFF1 = MAX - RMIN
506            IF (DIFF1 .LT. 20   ) GO TO 7004
507     C      ICNT = ICNT + 1
508     C      IF (ICNT .EQ. 2) GO TO 7015
509     C      GO TO 7004
510     C      GO TO 7015
511            GO TO 7004
512     7003   ICNT = 0
513     7004   OLDPRS = STORG(ISTCHK)
514     7005   ISTCHK = ISTCHK - 1
515            IF (ISTCHK .EQ. 0) ISTCHK = 200
516            COMPTR = COMPTR - NPARAM
517            IF (COMPTR .GE. 0) GO TO 7010
518            COMPTR = COMPTR + LRECL
519            COMREC = COMREC - 1
520     7010   CONTINUE
521     7015   CONTINUE
522            ICNT = 0
523            STADDR = COMREC * 10000. + COMPTR
524            IF (MNSTRT .LE. STADDR ) GO TO 7016
525            PKCNT = PKCNT - 1
526            GO TO 7017
527     C ----------
528     7016   PKREC(PKCNT) = COMREC
529            PKPTR(PKCNT) = COMPTR
530     C ** TRACE
531     C      WRITE (LUOUT,4220) PKCNT , COMREC , COMPTR ,PKREC1(PKCNT),
532     C    *      PKPTR1(PKCNT)
533     C      WRITE (1    ,4220) PKCNT , COMREC , COMPTR ,PKREC1(PKCNT),
534     C    *      PKPTR1(PKCNT)
535            DISTNC = 0
536     4220   FORMAT(/" START & STOP ",4I10," --- ",2I10)
537     C ** END
538     7017   MINFLW = 32767
539            GAPFLW = 0
540            RECNUM = SVREC
541            IPTR   = SVPTR
542            GO TO 5170
543     C
544     C      ***    IPASS = 2  PROCESS    ***
545     C      --------------------------------
546     C
547     C      IF MACHIN = 1 , THIS BREATH IS VENTILATOR FIRE.
548     C         THRESH IS THRESHOLD VALUE FOR MACHINE AIDED BREATH DETECTION
549     C         REFDAT IS REFERENCE DATA  FOR MACHINE AIDED BREATH DETECTION
550     C         MACHBR IS TOTAL NUMBER   OF  MACHINE AIDED BREATH
551     C
552     30810  CONTINUE
553            SVRESP = RESP
554            IF (RESP.LT.0)    RESP = 0
555     C .. MACHINE START
556            IF (RECNUM.EQ.VENREC .AND.
557          *     VENPTR.EQ.(IREF+IPTR))
558          *     GO TO 11051
559     C .. MACHINE STOP
560            IF (RECNUM .EQ. VENRE1 .AND.
561          *     VENPT1 .EQ. (IREF+IPTR) ) GO TO 7032
562     C
563            GO TO 12016
564     11051  CONTINUE
565     C      WRITE (LUOUT,7020) IFLOW, RECNUM, VENPTR
566     7020   FORMAT(/"MACHINE START ",4I5)
567            MACHIN = 1
568            VENRE1 = PKREC1(IFLOW)
```

```
869             VENPT1 = PKPTR1(IFLOW)
870             IFLOW = IFLOW + 1
871             IFLOW1 = IFLOW - 1
872             BASE = IDATA (IRESP+IPTR) * POLP
873             PRSVOL = 0
874             OLDVOL = 0
875             IF (IFLOW.GT.PKCNT) GO TO 11052
876             VENREC = PKREC(IFLOW)
877             VENPTR = PKPTR(IFLOW)
878                GO TO 12016
879     11052 VENREC = 32767
880             VENPTR = 32767
881                GO TO 12016
882       C
883       C  --  END OF MACHINE INSP BREATH
884     7232  CONTINUE
885             BASE = 30000
886             IF (STKPNT.EQ.0) GO TO 6279
887             DO 6270 IN =1,10
888     6270    PRSTAB(IN) = 0.0
889             PRSMAX = -32767
890             PRSMIN = 32767
891             DO 8055 IN =1,STKPNT
892       C     WRITE (1,7030) IN, SAVOL(IN,1),SAVOL(IN,2)
893     7030    FORMAT("VOL , PRS ",I5,2F10.1)
894             IF (SAVOL(IN,2) .LT. PRSMAX) GO TO 6271
895             MAXPOS = IN
896             PRSMAX = SAVOL(IN,2)
897     6271    CONTINUE
898             IF (SAVOL(IN,2) .GT. PRSMIN) GO TO 8055
899             PRSMIN = SAVOL(IN,2)
900     8055    CONTINUE
901             DELTA = PRSMAX - PRSMIN
902       C     WRITE (1,8060) STKPNT , PRSMAX , PRSMIN
903     8060  FORMAT(/3I10)
904             UNIT = DELTA / 10.0
905             DO 6272 IN =1,MAXPOS
906       C     IPOS = SAVOL(IN,2) / 2
907             IPOS = (SAVOL(IN,2) - PRSMIN) / UNIT + 0.5
908             IF (IPOS .GT. 10) IPOS = 10
909             IF (IPOS .LT. 1 ) IPOS = 1
910             PRSTAB(IPOS) = SAVOL(IN,1)
911     6272    CONTINUE
912             VENCNT = VENCNT + 1
913             SUMVEN = SUMVEN + PRSTAB(IPOS)
914             SQUVEN = SQUVEN + PRSTAB(IPOS) * PRSTAB(IPOS)
915       C     WRITE (4,6273) PRSTAB
916     6273  FORMAT(10F6.2)
917     6279  CONTINUE
918             STKPNT = 0
919     12016 CONTINUE
920       C
921       C  SUBTOT ... CUMULATIVE MINUTE TIDAL VOLUME
922       C  NDATA  ... BREATH INTERVAL COUNTR
923       C  BDUR   ... BREATH DURATION COUNTR
924       C  BBINT  ... BREATH-BREATH INTERVAL
925       C  BVOL   ... BREATH VOLUME
926       C  CUMVOL ... CUMULATIVE BREATH VOLUME
927       C
928       C  SUM   ** AREA FOR THE MINUTE RESP. INTEGRATION ---> BIAS LINE
929       C  SUBTOT ** AREA FOR SINGLE RESP. INTEGRATION   ---> TIDAL VOLUME
930       C  < REASON >   In 2ND PASS , MINute tidal volume cumulated after each
931       C               breath Because of  MINute last breath processing.
932       C
933             SUBTOT = SUBTOT + STEP * (RESP +OLDRSP)
934       C **  FOR PRESSURE CURVE
935             IF (BASE .EQ.30000) GO TO 6265
936             ACTVOL = POLP * IDATA (IRESP+IPTR) - BASE
937             PRSVOL = PRSVOL + STEP * (ACTVOL + OLDVOL)
938             PRSVO1 = PRSVOL * FCALIB
939             OLDVOL = ACTVOL
940             PRESS1 = IDATA (IREF+IPTR)
941             ACTPRS = PRESS1
942             STKPNT = STKPNT + 1
943             SAVOL (STKPNT,1) = PRSVO1
944             SAVOL (STKPNT,2) = ACTPRS
```

```
645   C        WRITE (1,7031) IDATA(IRESP+IPTR),STKPNT , PRSVO1 , ACTPRS
646   7031     FORMAT("VOL , PRS ",2I5,2F10.1)
647   6265     CONTINUE
648   C   **   FOR PRESSURE CURVE
649            NDATA = NDATA + 1
650            IF (RESP.LE.0) GO TO 6130
651   C
652   C *
653            BDUR = BDUR + 1
654            IF (AMPL.GT.RERESP) GO TO 6130
655            AMPL = RERESP
656   6130     CONTINUE
657            IF (AMPMIN .GT. RERESP ) AMPMIN = RERESP
658   C
659   C
660            IF((RESP*OLDRSP).GT.0) GO TO 5170
661   C   IF TWO SUCCESSIVE POINTS HAVE DIFFERNT SIGN ,
662   C        THEN END OF BREATH ENCOUNTRED .
663   C
664   C
665            IF (OLDRSP .GT. 0) GO TO 215
666            SGNCNT = SGNCNT + 1
667            IF (SGNCNT.LT.3) GO TO 215
668            GO TO 5170
669   C
670   C        ( SIGN MUST CHANGE FROM + TO - FOR BREATH PATTERN)
671   C
672   C        CHECK THE CRTITERIA OF VALID BREATHING
673   C        ----------------------------------------
674   C
675   215      CONTINUE
676   C
677   C
678            BDUR1 = BDUR * SAMPLE
679            SUBT1 = SUBTOT * FCALIB
680            IF (AMPL .LE. AMPMIN) GO TO 5070
681            DIST  = AMPL   - AMPMIN
682            IF (DIST.LT.10) DSTCNT = DSTCNT + 1
683   C
684            IF ((BDUR*SAMPLE) .LE. CRDUR) GO TO 5070
685            IF ((SUBTOT*FCALIB).LE.CRVOL) GO TO 5070
686            IF (DIST.LT.10)                GO TO 5070
687   C
688   C
689   C *      NOISE CRITERIA PASSED      *
690   C        (VALID BREATH PROCESS)
691   C
692            NBRETH = NBRETH + 1
693            SGNCNT = 0
694            NLIMIT = 0
695            SUM = SUM + SUBTOT
696            SUBSUM = SUBTOT * FCALIB
697            ALLSUM = SUM    * FCALIB
698            BBINT       =(NDATA - 1) * SAMPLE
699            IF (RESP .EQ. 0) BBINT = NDATA * SAMPLE
700            BVOL           = SUBSUM
701            CUMVOL         = ALLSUM
702            BDURTM         = BDUR * SAMPLE
703   C
704   C *      MACHINE AIDED BREATH PROCESS   *
705   C
706            IF (MACHIN.EQ.0) GO TO 12020
707               MACHBR = MACHBR + 1
708               MACSUM = MACSUM + BVOL
709               SQUMAC = SQUMAC + BVOL * BVOL
710               NBRETH = NBRETH - 1
711               SUM = SUM - SUBTOT
712               MACHIN = 0
713               CUMVOL = SUM * FCALIB
714               VENAMP = VENAMP + AMPL
715               GO TO 12030
716   C *
717   12020    NTAB = NTAB + 1
718            IF (NTAB.GT.120) WRITE (1,31300) RECNUM
719   31300    FORMAT(/"TABLE INDEX IS OVER 120 "/
```

```
720              *  "PLEASE STOP THE RUN !!!!!! ")
721              IF (NTAB.GT.120) PAUSE 120
722           TABL(1,NTAB) = BBINT
723           TABL(2,NTAB) = BVOL
724           TABL(3,NTAB) = BDURTM
725           TABL(4,NTAB) = AMPL
726           TABL(5,NTAB) = COUNTR
727           TABL(6,NTAB) = RECNUM
728              SUMDUR = SUMDUR + BDURTM
729              SUMVOL = SUMVOL + BVOL
730              SUMAMP = SUMAMP + AMPL
731              SQUDUR = SQUDUR + BDURTM * BDURTM
732              SQUVOL = SQUVOL + BVOL * BVOL
733              SQUAMP = SQUAMP + AMPL * AMPL
734              OLDAMP = AMPL
735     12030 CONTINUE
736              BDRSUM = BDRSUM + BDUR
737              BDUR = 0
738              AMPL = -1000
739              AMPMIN = 32767
740              SUBTOT = 0
741              NDATA = 1
742        C     STKPNT = 0
743        C *   GO TO NEXT DATA PROCESSING
744              GO TO 5170
745        C
746     5070          CONTINUE
747        C
748        C     INVALID BREATH PROCESSING
749        C     -------------------------
750        C
751              TOTCNT = TOTCNT + 1
752              AMPL = -1000
753              AMPMIN = 32767
754              BDUR = 0
755              SUBTOT = 0
756              SGNCNT = 0
757        C     STKPNT = 0
758        C
759     5170          CONTINUE
760        C
761        C *   UPDATE RESP DATA TO THE CURRENT POINT *
762        C
763              IF (SGNCNT.EQ.0) OLDRSP = RESP
764              OLDFLW = FLOW
765        C
766        C     PROCESS THE TIME CODE & INTEGRATION COUNTR
767        C
768              IF(ITCR.EQ.0 .OR. IPASS.EQ.1) GO TO 230
769        C --  PROCESS TIME FROM TIME CODE GENERATOR
770              ITEMP = IDATA(ITCR+IPTR)
771              IF(ITEMP.LE.0) GO TO 230
772              CALL CLOCK(ITEMP,IFLAG,ITIME,INITTC)
773        C
774        C --  CHECK THE TIME FOR THE MINUTE STATISTICS
775        C        NMDATA ... DATA # FOR 1 MINUTE
776        C        COUNTR ... CURRENT DATA COUNT
777        C
778     230    COUNTR = COUNTR+1
779              IF (IPASS.EQ.2) GO TO 7021
780                IF (COUNTR .GT. NMDAT1 ) GO TO 240
781                GO TO 7022
782     7021      IF (COUNTR .GT. NMDATA ) GO TO 240
783     7022   CONTINUE
784        C
785        C --  IF COUNTR > NMDATA , GO TO PRINT-MINUTE-STATISTICS
786     232    IPTR = IPTR+NPARAM
787        C
788              IF(IPTR-LRECL) 235,204,204
789     235      IF (INIT.EQ.0) GO TO 207
790              IF (INIT.EQ.1) GO TO 210
791        C --  IF IPTR > LRECL , GO TO READ-NEXT-RECORD.
792        C
793        C ........................................................
794        C I   END OF TIME PERIOD (MINUTE)                          I
795        C I      PRINT THE MINUTE STATISTICS  ON THE SCREEN AND PRINTER I
796        C I      WRITE MINUTE BABY.S PURE BREATHS ON THE LU 5(RIGHT CART.)I
```

```
797    C !    WRITE MINUTE VENT,S FIRE           ON THE LU 4(LEFT. CART.)!
798    C ......................................................................
799    C
800    C --  UPDATE THE TIME IF NOT USING THE TIME CODE SIGNAL
801    240   CONTINUE
802          IF (IPASS.EQ.1) GO TO 260
803          IF(ITCR.NE.0) GO TO 260
804          ITIME(4) = ITIME(4)+PERIOD
805          ITMAX = 60
806          DO 255 I=4,2,-1
807          IF(I.EQ.2) ITMAX = 24
808    252   IF(ITIME(I).LT.ITMAX) GO TO 255
809          ITIME(I) = ITIME(I)-ITMAX
810          ITIME(I-1) = ITIME(I-1)+1
811          GO TO 252
812    255   CONTINUE
813    C -----------------------------------------------------------------------
814    C I    IN PASS 1 , COMPUTE THE BIAS LINE BY INTEGRATION OF RESP SIGNAL. I
815    C I    IN PASS 2 , PROCESS AND STORE MINUTE STATS. ON DISK & ON CONSOLE, I
816    C I              STORE VENTILATOR BREATHS (MIN) ON CT4,                 I
817    C I              STORE BABY BREATHS (MIN) ON CT5 .                      I
818    C I              COMPUTE THE CRITERIA FOR NEXT MINUTE                   I
819    C -----------------------------------------------------------------------
820    260   GO TO (261,262),IPASS
821    C --  PASS = 1
822    261   BIAS = SUM/PERIOD
823          IF (MIN1.LT.2) GO TO 2611
824          IF (ABS(BIAS-OLBIAS).GE.10) BIAS = OLBIAS
825    2611  OLBIAS = BIAS
826          GO TO 11285
827    C
828    C
829    262   CONTINUE
830    C
831    C     PASS = 2
832    C
833    C *   WRITE   MINUTE VOLUME ON PRINTER , LU 4 AND LU 5
834    C
835          AVRDUR = SUMDUR / NBRETH
836          AVRVOL = SUMVOL / NBRETH
837          AVRAMP = SUMAMP / NBRETH
838          VARDUR = (SQUDUR-SUMDUR*SUMDUR/NBRETH) / (NBRETH-1)
839          VARVOL = (SQUVOL-SUMVOL*SUMVOL/NBRETH) / (NBRETH-1)
840          VARAMP = (SQUAMP-SUMAMP*SUMAMP/NBRETH) / (NBRETH-1)
841          STDDUR = SQRT(VARDUR)
842          STDVOL = SQRT(VARVOL)
843          STDAMP = SQRT(VARAMP)
844    C     CRDUR = AVRDUR - 3.0 * (STDDUR / SQRT(1.0*NBRETH))
845    C     CRVOL = AVRVOL - 3.0 * (STDVOL / SQRT(1.0*NBRETH))
846          CRVOL = AVRVOL - STDVOL
847          CRDUR = AVRDUR - STDDUR
848          AVRVEN = VENAMP / MACHBR
849          IF (MACHBR.EQ.0) AVRVEN = 0
850          TORR   = (AVRVEN - BIAS) * 0.15
851          IF (AVRVEN.EQ.0) TORR = 10
852          CRAMP = BIAS   + TORR
853    C0503 CRAMP = AVRAMP - 2.56 * (STDAMP / SQRT(1.0*NBRETH))
854          IF (CRDUR.LT.MINDUR) CRDUR = MINDUR
855          IF (CRDUR.GT.0.5) CRDUR = .5
856          IF (CRVOL.LT.MINVOL) CRVOL = MINVOL
857    C0503 IF (CRAMP.GT.3.0) CRAMP = 3.0
858    C0503 IF (CRAMP.LT.1.0) CRAMP = 1.0
859          IF (CRVOL.GT.1.0) CRVOL = 1.0
860    C
861    C *
862    C
863          CUMVOL = 0
864          VENAMP = 0
865          NVALID = 0
866          IF (NBRETH.EQ.0) GO TO 11284
867          SUMINT = 0
868          DO 11205 I = 1,NBRETH
869          IF (TABL(2,I) .LE. CRVOL ) VOLCNT = VOLCNT + 1
870          IF (TABL(3,I) .LE. CRDUR ) DURCNT = DURCNT + 1
871          IF (TABL(4,I) .LE. CRAMP ) AMPCNT = AMPCNT + 1
872          IF (TABL(2,I) .LE. CRVOL   .OR.
873        *    TABL(4,I) .LE. CRAMP   .OR.
```

```
874  *      TABL(3,I) .LE. CRDUR ) GO TO 11202
875         GO TO 11203
876  11202  TABL(2,I) = 0
877         SUMINT = SUMINT + TABL(1,I)
878         TOTCNT = TOTCNT + 1
879         GO TO 11205
880  11203  CONTINUE
881         TABL(1,I) = TABL(1,I) + SUMINT
882         SUMINT = 0
883  11205  CONTINUE
884         DO 12831 I = 1,NBRETH
885         IF (TABL(2,I).EQ.0) GO TO 12831
886         NVALID = NVALID + 1
887         CUMVOL = TABL(2,I) + CUMVOL
888         SECOND = TABL(5,I) * SAMPLE
889         WRITE (7,5205) TABL(1,I) , TABL(2,I) , CUMVOL ,
890       *                TABL(3,I) , TABL(4,I) ,
891       *                ITIME(2) , ITIME(3) , SECOND
892       *               ,TABL(6,I)
893  12831 CONTINUE
894        NBRETH = NVALID
895  C
896  C *
897  C
898  11284 OUTCNT = OUTCNT + NBRETH
899        WRITE(LUOUT,264)(ITIME(I),I=2,3),CUMVOL,MACSUM,BIAS,NBRETH
900      *       ,MACHBR ,CRDUR , CRVOL, CRAMP
901        WRITE(5,11281) CUMVOL,NBRETH,RECNUM
902  11281 FORMAT(2F10.4,I10)
903        BIAS = 0
904        NTAB = 0
905        CRVOL = MINVOL
906        CRDUR = MINDUR
907        FLWDST = SAVFLW
908        DISTNC = SDSTNC
909  C     IF (VENCNT .EQ. 0) GO TO 7035
910  C     AVRVEN = SUMVEN / VENCNT
911  C     STDVEN = (SQUVEN - SUMVEN * SUMVEN / VENCNT) / (VENCNT - 1)
912  C     STDVEN = SQRT (STDVEN)
913  C     WRITE (LUOUT,7034) AVRVEN , STDVEN
914  7034  FORMAT(19X,2G8.4/)
915  C     WRITE(4,6273)ITIME(2),ITIME(3),MACSUM,VENCNT,AVRVEN,STDVEN
916  C   *       ,IDUMMY
917        IF (MACHBR .EQ. 0) GO TO 8080
918        AVRMAC = MACSUM / MACHBR
919        STDMAC = (SQUMAC - MACSUM * MACSUM / MACHBR)
920        STDMAC = SQRT (STDMAC)
921        WRITE (4,8078) ITIME(2) , ITIME(3),VENCNT,AVRMAC,STDMAC
922  8078  FORMAT( 3I10 , 2F10.1)
923  8080  CONTINUE
924        SUMVEN = 0.0
925        SQUVEN = 0.0
926        VENCNT = 0
927  7035  CONTINUE
928  C
929  C
930  C     RESET COUNTRS
931  C     -------------
932  C
933  11285 COUNTR = 1
934        INIT = 0
935        SUM = 0.
936        AMPL = -1000
937        AMPMIN = 32767
938        MACHBR = 0
939        MACSUM = 0
940        SQUMAC = 0
941        IFLOW = 0
942        SUMDUR = 0
943        SUMVOL = 0
944        SUMAMP = 0
945        SQUDUR = 0
946        SQUVOL = 0
947        SQUAMP = 0
948        IF(IPASS.EQ.2) GO TO 31165
949        IF (PKCNT .EQ.0) GO TO 31162
```

```
950            IFLOW = 1
951            VENREC = PKREC(1)
952            VENPTR = PKPTR(1)
953            VENPT1 = PKPTR1(1)
954            VENRE1 = PKREC1(1)
955            GO TO 270
956     31162  VENREC = 32767
957            VENPTR = 32767
958     C
959     31165  CONTINUE
960            PKCNT = 0
961            IBR = NBRETH
962            NBRETH = 0
963            INIT = 0
964            IF (IPASS.EQ.1) SAVE1 = DATA
965            IF (IPASS.EQ.2) SAVE2 = DATA
966     270    CONTINUE
967            MIN1 = MINUTE - 1
968            IF(IPASS.EQ.2) WRITE(1,5090) ITIME(2),ITIME(3) ,IBR,CUMVOL
969     5090   FORMAT((I2,":",I2)," BREATH "," COUNT = ",I5,5X,F10.2,"CC")
970            IPASS = IPASS + 1
971            IF (IPASS.EQ.3) IPASS = 1
972            IF (IPASS.EQ.2) MINUTE = MINUTE + 1
973     C
974     C * GO TO "CHECK FOR END OF RECORD & PROCESS AGAIN ROUTINE"
975            GO TO 232
976     C
977     310    CONTINUE
978            MIN1 = MINUTE - 1
979            WRITE(LUOUT,312)MIN1   ,OUTCNT
980     399    CALL CLOSE(IDCB)
981            CALL CLOSL(7,IERR)
982            WRITE (4,6273) IDUMMY,ENDMRK,ENDMRK,ENDMRK
983            CALL CLOSL(4,IERR)
984            CALL CLOSL(5,IERR)
985     C
986     C * CRITERIA ERROR STATISTICS
987            WRITE (LUOUT,4233) TOTCNT,DURCNT,VOLCNT,AMPCNT,DSTCNT
988     4233   FORMAT(/" TOTAL REJECTED BREATHS = ",I5/
989        *          " DURCNT = ",I5,5X,"VOLCNT = ",I5/
990        *          " AMPCNT = ",I5,5X,"DSTCNT = ",I5)
991            PVOL = VOLCNT / TOTCNT * 100
992            PDUR = DURCNT / TOTCNT * 100
993            PAMP = AMPCNT / TOTCNT * 100
994            PDIST = DSTCNT / TOTCNT * 100
995            WRITE (LUOUT,6041) PVOL , PDUR , PAMP , PDIST
996     6041   FORMAT(///"% OF REJECTED BREATHS"//5X," % VOL = ",F5.1//
997        *            5X," % DUR = ",F5.1/
998        *            5X," % AMP = ",F5.1/
999        *            5X," % DST = ",F5.1/)
1000           STOP
1001    C
1002    C      ERROR HANDLING
1003    C
1004    920    IF(LEN.EQ.-1) GO TO 920
1005    901    WRITE(1,902) IERR
1006           GO TO 999
1007    920    WRITE(1,922)
1008           GO TO 999
1009    999    CALL CLOSE(IDCB)
1010           STOP 7777
1011    C
1012    C      FORMAT STATEMENTS
1013    C
1014    10     FORMAT(2/,"TIDAL:   TIDAL VOLUME COMPUTATION",2/,
1015        1   "DATAFILE NAMR, LRECL [2000 MAX], # PARAMETERS?  _")
1016    12     FORMAT(40A2)
1017    20     FORMAT(/"PARAMETER # FOR PNEUMOTACH?  _")
1018    22     FORMAT(/"PNEUMOTACH POLARITY? [+ or -]  _")
1019    23     FORMAT(A1)
1020    24     FORMAT(/"PARAMETER # FOR SLOW CODE?  _")
1021    26     FORMAT(/"INTEGRATION PERIOD, SAMPLING INTERVAL? [SEC]  _")
1022    30     FORMAT(/"ENTER CAL. FACTOR: (0 IF UNKNOWN)  _")
1023    34     FORMAT(/"TOTAL CALIBRATION VOLUME?  _")
1024    36     FORMAT(/"STARTING REC #, ENDING REC # FOR CALIBRATION?  _")
1025    38     FORMAT(/"FIND CAL. FACTOR ONLY [YES / NO]?  _")
1026    40     FORMAT(/"OUTPUT FILE NAMR?  _")
```

```
1727     60    FORMAT(/"STARTING RECORD #,  # OF RECORDS TO PROCESS?",
1728           1  /,"  [# RECORDS < 1 FOR WHOLE FILE]",10X,"_")
1729     65    FORMAT(/"ENTER COMMENTS [80 CHAR. MAX.]")
1730     92    FORMAT(/"CAL FACTOR =",G10.4," FOR TEST CALIBRATION OF",
1731           1  F5.0," cc.")
1732    158    FORMAT(/"NUBRN:  NOT ABLE TO DECODE SLOW CODE.")
1733    264    FORMAT(5X,I2,":",I2,3X,6X,2G8.4,3X,G10.2,I4,2X,I4
1734           *,5X,F3.1,F5.1,I5)
1735    266    FORMAT(3I3,1X,G10.4)
1736    268    FORMAT(G12.4)
1737    304    FORMAT("1",2/,10X,I2,":",I2,4X,I2,
1738           1  "/",I2,"/",I2,5/,10X,40A2,5/,10X,
1739           2  "FILE/LU#: ",3A2,10X,"RECORD LENGTH (WORDS):",
1740           3  I5,10X,"           ",I3,3/,10X,
1741           4  "STARTING RECORD:",I5,10X,"# RECORDS PROCESSED:",I5,
1742           5  4/,10X,"INTEGRATION PERIOD :",F5.0," SEC.",5X,
1743           6  "CAL. FACTOR =",G12.4/,11X," SAMPLING RATE     :",
1744           6  F5.2," SEC.")
1745   3041    FORMAT(4/,7X,"TIME",5X,"TIDAL VOLUME (cc.)",5X,"BIAS",5X,
1746           *"BREATH/MIN.",6X,"CRITERIA"/
1747           */5X,8"-",3X,18"-",2X,10"-",2X,10"-",5X,13"-")
1748    312    FORMAT(/////,"      PROCESSED MINUTES = ",I7,
1749           *          //,"      ALL BREATHS COUNT = ",F7.0)
1750    322    FORMAT(/"TIDAL:  TMP ERROR =",I4)
1751    322    FORMAT(/"TIDAL:  EOF FOUND")
1752   3205    FORMAT(5F5.1,5X,I2,":",I2,":",F5.1 ,110, 5X,I5)
1753   3206    FORMAT(8F10.3)
1754           END
1755    S
```

I claim:

1. An apparatus for obtaining continuous measurements of infant ventilation during assisted ventilation by an assisted ventilation gas source comprising:
   a plethysmograph having means for maintaining a predetermined body temperature of an infant placed therein and having at least an input port,
   means for coupling an assisted ventilation gas source to said input port of said plethysmograph,
   an endotracheal tube having one end coupled to said input port and the other end adapted for insertion into the ariwway of an infant placed in said plethysmograph such that said airway is isolated from the interior of said plethysmograph,
   a pneumotachometer coupled to said plethysmograph adapted for sensing pressure changes occurring on the interior of said plethysmograph,
   a differential pressure transducer coupled to said pneumotachometer for outputting a flow signal reflecting pressure changes inside said plethysmograph,
   means for detecting pressure changes in said endotracheal tube caused by said assisted ventilation gas source and breathing efforts of said infant and for outputting a pressure signal in accordance with such pressure changes,
   means for outputting time data indicating the current time, and
   a preprogrammed computer system having means for receiving said pressure and flow signals and said time data for converting said pressure and flow signals into digital data and for determining from said digital data and said time data at least whether pressure changes in the interior of said plethysmograph are due to assisted ventilation or to the infant's breathing efforts.

2. The apparatus of claim 1 wherein said means for detecting pressure changes caused by said assisted ventilation gas source and breathing efforts of said infant comprises a pressure transducer adapted for sensing pressure in said endotracheal tube.

3. The apparatus of claim 2 wherein said pneumotachometer is positioned inside said plethysmograph.

4. The apparatus of claim 3 further comprising:
   recording means for recording said pressure, flow and time data, and
   means for coupling data from said recording means to said preprogrammed computer system.

5. The apparatus of claim 1 wherein said preprogrammed computer system receives and digitizes said pressure and flow signals in real-time.

6. An apparatus for obtaining continuous measurements of infant ventilation during assisted ventilation by an assisted ventilation gas source comprising:
   a plethysmograph having means for maintaining a predetermined body temperature of an infant placed therein and having at least an input port,
   means for coupling an assisted ventilation gas source to said input port of said plethysmograph,
   an endotracheal tube having one end coupled to said input port and the other end adapted for insertion into the airway of an infant placed in said plethysmograph such that said airway is isolated from the interior of said plethysmograph,
   a first pneumotachometer coupled to said plethysmograph adapted from sensing pressure changes occurring on the interior of said plethysmograph,
   a differential pressure transducer coupled to said pneumotachometer for outputting a flow signal reflecting pressure changes inside said plethysmograph,
   a second pneumotachometer coupled to an exhaust port of said assisted ventilation gas source,
   a second pressure transducer coupled to said second pneumotachometer for outputting a gas source pressure signal reflecting output of said assisted ventilation gas source,
   means for outputting time data indicating the current time, and
   a preprogrammed computer system having means for receiving said pressure and flow signals and said time data, for converting said gas source pressure and flow signals into digital data and for determining from said digital data and said time data at least whether pressure changes in the interior of said plethysmograph are due to assisted ventilation or to the infant's breathing efforts.

7. A method for discriminating breaths caused by a ventilator from breaths due to the respiratory efforts of an infant on assisted ventilation, where said infant is located in a plethysmograph and receives gas from said ventilator via endotracheal tube which is isolated from the interior of the plethysmograph comprising the steps of:
- determining the volume of gas flowing into said plethysmograph during a ventilator or an infant breath,
- determining the pressure in said endotracheal tube during the period of said breath,
- determining whether said pressure in said endotracheal tube exceeded a predetermined magnitude, and
- updating a first counter for ventilator breaths if said pressure is greater than said predetermined magnitude and, if it is not, updating a second counter for infant breaths.

8. The method of claim 7 further comprising the step of:
- calculating the volume, duration and maximum amplitude of said breath,
- storing said volume, duration and maximum amplitude in a file for ventilator breaths if said pressure is greater than said predetermined magnitude and, if it is not, storing said volume, duration and maximum amplitude in a file for infant breaths.

9. The method of claim 7 wherein the steps of determining the volume of gas flowing into said plethysmograph during an infant or a machine breath comprises the steps of:
- computing a calibration factor,
- integrating inspiratory flow data obtained for a predetermined period, and
- multiplying the result of integrating said inspiratory flow data by said calibration factor.

10. The method of claim 9 wherein the step of computing a calibration factor comprises:
- over a predetermined calibration period, injecting a predetermined volume of gas into said plethysmograph and withdrawing said predetermined volume, while the infant to be monitored is present in said plethysmograph with said predetermined volume of gas sufficiently large such that the volume of gas flowing into said plethysmograph on account of infant and machine breaths during said predetermined calibration period comprises a relatively small percentage of the total volume of gas flowing into said plethysmograph during said predetermined calculation period,
- sampling at a predetermined sampling rate, flow data values derived from a means for measuring gas volume flowing into and out of said plethysmograph during said predetermined period,
- integrating those flow data values reflecting gas flow into said plethysmograph to derive a flow data value integration,
- obtaining a real-time bias value by dividing said flow data value integration by the product of said predetermined sampling rate and the number of samples obtained during said predetermined sampling period,
- obtaining an adjusted inspiratory volume by integration using in an integration calculation those flow data values reflecting gas flow into said plethysmograph, with each of those flow data values reflecting gas flow into said plethysmograph having said real-time bias value subtracted from it prior to being included in said integration calculation, and
- dividing a numeric value representing said predetermined volume of gas by said adjusted inspiratory volume to determine said calibration factor.

* * * * *